United States Patent [19]

Maroko

[11] Patent Number: 4,980,344
[45] Date of Patent: Dec. 25, 1990

[54] COMPOSITIONS FOR IMPROVING CIRCULATORY PERFORMANCE

[76] Inventor: Peter R. Maroko, 1765 Garwood Dr., Cherry Hill, N.J. 08003

[21] Appl. No.: 203,480

[22] Filed: Jun. 6, 1988

Related U.S. Application Data

[63] Continuation-in-part of Ser. No. 797,788, Nov. 13, 1985, Pat. No. 4,749,708, which is a continuation of Ser. No. 578,955, Feb. 10, 1984, abandoned, and a continuation of Ser. No. 788,507, Oct. 18, 1985, Pat. No. 4,761,417, which is a continuation of Ser. No. 378,122, May 14, 1982, abandoned.

[51] Int. Cl.$^5$ .................... A61K 31/675; A61K 31/44
[52] U.S. Cl. ...................................... 514/26; 514/280; 514/284
[58] Field of Search .......................... 514/280, 284, 26

[56] References Cited

U.S. PATENT DOCUMENTS

| | | | |
|---|---|---|---|
| 3,272,707 | 9/1966 | Tedeschi | 546/48 |
| 3,884,911 | 5/1977 | Shimada et al. | 546/48 |
| 3,894,027 | 7/1975 | Sohar et al. | 546/149 |
| 3,910,938 | 10/1975 | Ikekawa et al. | 546/48 |
| 3,933,826 | 1/1976 | Kametani | 546/71 |

FOREIGN PATENT DOCUMENTS

| | | | |
|---|---|---|---|
| 2356654 | 11/1973 | Fed. Rep. of Germany | 546/76 |
| 14700 | 2/1973 | Japan | 546/71 |
| 0101399 | 8/1975 | Japan | 546/71 |

OTHER PUBLICATIONS

Kulkarni et al.—Japan J. Pharmacol. 22, 11–16 (1972).
*Chemical & Pharmaceutical Bulletin*, vol. 18, No. 7, Jul. 1970, pp. 1299–1304 (Fukuda et al.).
Jang—*J. Pharmacol Exp. Ther.*, 71:178–186, 1941.
*Comptes Rendus Societe de Biologie*, 127; 1938, pp. 1022–1024 (Mercier).
Soto et al.—*Rev. Assoc. Med. Argent*, 41:3062–3068 (1933).
Soto et al.—*Rev. Assoc. Med Argent*, 47, 2498–2501 (1933).
Chopra et al.—Ind. Jour. Med. Res., XIX 4, Apr. 1932.

*Primary Examiner*—Frederick E. Waddell
*Attorney, Agent, or Firm*—Weiser & Stapler

[57] ABSTRACT

Compositions having a compound from the family of protoberberines, especially coreximine, are used in conjunction with a cardiac glycoside. The composition and therapeutic method of administering the composition, orally and otherwise, increases the contractility of the heart as shown by a positive inotropic effect. The positive inotropic effect is observed over a wide therapeutic index.

15 Claims, No Drawings

COMPOSITIONS FOR IMPROVING CIRCULATORY PERFORMANCE

This is a continuation-in-part application of application Ser. No. 797,788 filed Nov. 13, 1985, now U.S. Pat. No. 4,749,708 which is a continuation of application Ser. No. 578,955 filed Feb. 10, 1984 now abandoned, and of pending application Ser. No. 788,507 filed Oct. 18, 1985, which is a continuation of application Ser. No. 378,122 filed May 14, 1982 now abandoned, which pending application is incorporated herein in its entirety, and which application has now issued as U.S. Pat. No. 4,761,417.

In the parent application, there were disclosed various protoberberine compounds which are useful in the treatment of various cardiovascular diseases. The disclosure of the parent case is incorporated herein by reference.

In accordance with the invention of the parent application, there were disclosed and encompassed therein various biologically active derivatives of these protoberberine compounds, including metabolites. Within the contemplation of the parent case, were also compounds which have various degrees and/or positions of unsaturation of the rings. Isomers were also disclosed.

The present invention deals with several compounds of the protoberberine family, especially those protoberberines which have special qualities including a positive inotropic effect and the property to improve aortic blood flow, and cardiac output, and the property to affect the heart rate, the systemic arterial pressure, the afterload of the left ventricle, the preload of the left ventricle, the calculated vessel peripheral resistance, the mean arterial pressure, and heart arrhythmias.

The invention also deals with componds which are particularly attractive because they are more effective orally than other of this class of protoberberines.

It has now been found that within this class of compounds there is a relatively wide spectrum of activity and that in some of the compounds the positive inotropic properties are not significant enough to be detected, while other compounds do exhibit this property to varying degrees. At the same time, these compounds have varying effects on the heart rate, vasodilation, cardiac output and anti-arrhythmic effect. These aspects are described in greater detail hereinafter.

The invention also relates to other biochemical or biomedical applications. The other aspects, to which the invention relates, will become apparent to one of average skill in the art from the teaching herein.

One important, but not the only important field to which the invention relates is the cardiovascular field, both in humans and animals. Today cardiovascular diseases, which have reached epidemic proportions, account for a very high proportion of all deaths in the world, especially in industrialized nations. Approximately one of every five persons has some form of cardiovascular ailment such as heart disease, cerebrovascular disease or hypertension.

Cardiovascular disease not only is fatal, but causes prolonged suffering and disability in even a larger proportion of the population. In the United States alone, cardiovascular disease was responsible for almost one million fatalities in 1979, well over one-half of all reported deaths. Almost 5 million person afflicted with cardiovascular disease are hospitalized annually. The cost of this disease in terms of human annual costs due to morbidity amount to over 8 billion dollars. Braunwald, *Heart Disease, A Textbook of Cardiovascular Medicine,* W. B. Saunders Company, Philadelphia, 1980 ("Braunwald") which is incorporated herein by reference. For further details relating to disorders of the heart, reference is made to *Harrison's Principles of Internal Medicine,* Thorne, Adams, Braunwald, Isselbacher and Petersdorf, McGraw-Hill Book Company, 8th Ed., Part 7, ("Harrison's") *Disease of the Organ Systems, Disorder of the Heart,* Chap. 231 through 248, which are referred to specifically herein and incorporated herein by reference.

Reference shall also be made herein to the following clinical books, namely, *Veterinary Pharmacology and Therapeutics,* Jones, Booth and McDonald, Iowa State University Press, 4th Ed., 1977; Physicians' Desk Reference "PDR" Medical Economics Company, 36th Ed., 1982; and *Veterinary Pharmaceuticals and Biologicals,* "VPB", 1980/1981, Aronson, Harwal Publishing Company, Media, Pa., 1980.

The direct cardiac action of drugs may be divided into four major areas: (1) an effect on contractility (inotropic effect), reflecting alterations in the myocardial force-velocity relation at any given initial muscle length; (2) an effect on heart rate expressed as an alteration in the rhythmicity, i.e., the frequency of discharge of normal pacemaker tissue, generally in the sinoatrial node; (3) an effect on conductivity, i.e., on the velocity with which the depolarization wave travels through the myocardium and the atrial ventricular conductive system; (4) an effect on irritability, i.e. the tendency to provoke ectopic pacemaker activity, which is dependent on the rate of diastolic depolarization and the threshold potential.

One of the most serious consequences of all types of cardiovascular diseases involves the pathophysilogical state in which the heart fails in its prime function as a muscle acting as a pump. In general, heart failure is the result of severe primary depression of myocardial contractility or extreme ventricular hemodynamic overload combined with secondary diminution of the contractile state. For a description of the basics and disorders of the myocardial function, especially cardiac contraction see *Harrison's* chapter 236.

Knowledge of the biochemical and physiological changes in heart failure has advanced considerably in recent years. Unfortunately, the development of pharmacological agents with clinically useful positive properties on cardiac contractility (positive inotropic agents) has not kept pace.

A large number of compounds have as their major pharmacological action the ability to alter cardiovascular function. The therapy of cardiac diseases, independently of the etiology of these diseases, is aimed either to compensate the mechanical dysfunction of the heart which is the deterioration of the function of the heart as a pump (and is called heart failure); or treatment of the abnormal electrical stimuli (i.e. arrhythmias), which may cause a life threatening condition. The therapy of the latter is antiar-rhythmic treatment. The most commonly used drugs are quinidine and procainamide. The treatment of cardiac arrhythmias can also be performed by propranolol, a beta-adrenergic blocking agent. Some other new antiarrhythmic agents are being either introduced or tested now. To treat the former condition (i.e. any form of heart pump failure) digitalis and certain other structurally closely allied drugs have in common a specific and powerful action on the myocardium that is unrivaled for the treatment of congestive heart failure.

More recently vasodilators have been proposed (perhaps to overcome or compensate a principal shortcoming of digitalis), to treat heart failure in a different manner, i.e. by reducing the afterload and thus improving performance not through a positive inotropic mechanism. These agents also reduce the preload (generally measured by left ventricular end diastolic pressure or pulmonary wedge pressure) which is generally elevated in patients with congestive heart failure.

With respect to cardiac disorders, depression of ventricular function is the principal cause of heart failure, and improvement of myocardial contractility by means of cardiacally active glycosides have been the keystone in the management of this pathologic condition in humans and animals. These glycosides are typically represented by digitalis glycosides since these are the most commonly used, although other glycosides are equally active such as ouabain which is a stophantic glycoside. However, normally the generic term used (albeit somewhat incorrectly) is digitalis. Indeed, despite the value of diuretics and afterload-reducing agents, the glycosides remain the principal positive inotropic agents useful in long-term management of patients with congestive heart failure. Other drugs, known to act through stimulation of myocardial beta-adrenergic receptors such as the catecholamines and sympathomimetic agents, are very potent cardiac stimulants, but for the most part may have serious adverse effects, such as tachycardia, ventricular irritability and intensification of myocardial ischemia. Their use is restricted mainly to in-hospital intravenous treatment of cardiac shock and they are not given orally for chronic congestive heart failure. A major therapeutic advance in the medical treatment of congestive heart failure awaits discovery; namely, an effective, non-toxic drug that increases myocardial contractility without adverse effects such as increase in peripheral vascular resistance, decrease in coronary flow, arrhythmias and a treatment that is free of the adverse effect of digitalis.

It is an object of this invention to provide a class of compounds which have a combination of advantageous properties over digitalis (and other cardiac glycosides).

It is a further object of the invention to provide a new class of compounds which may be designated generically as protoberberine alkaloids which are positive inotropic agents which are accompanied with other desirable properties.

It is another object of the invention to provide a berberine-type compound (and pharmaceutical composition which include same) which acts on the mammal cardiac system differently or has different effects, than reported previously with natural or other "berberine".

Other objects of the invention will become apparent from the following disclosure.

In accordance with the invention, a group of protoberberine alkaloids and derivatives has been discovered which is found to exert a strong positive inotropic action, decrease peripheral vascular resistance, raise cardiac output, and is virtually free of the drawbacks of digitalis such as arrhythmias. The compounds of the invention have a significantly broader therapeutic ratio than digitalis type cardiac glycosides.

The compounds and biologically active compositions of the invention are useful for the treatment of congestive or chronic heart failure and also acute heart failure and/or cardiogenic shock. Moreover, states of systemic arterial hypotension, low cardiac output and shock of other origins with increase peripheral vascular resistance and/or decreased cardiac output will also benefit from this therapy.

The invention which has several embodiments to which some were referred to above; others are briefly described below; others will become apparent as the description proceeds.

An embodiment of the invention relates to isoquinoline, especially protoberberine, alkaloids, their compositions which have a biological effect, especially in the treatment of cardiovascular disorders, heart failure, cardiac arrhythmias, and shocks of circulatory nature, by affecting flow, heart rate, systemic arterial pressure, afterload of the left ventricle, preload in the left ventricle, calculated vessel peripheral resistance, mean arterial pressure and arrhythmias. These effects may be obtained to varying degrees, concurrently or not, with the individual compounds (compositions and methods of use) of the invention.

Another embodiment is the administration of a compound of the invention with the main objective to treat those patients who will benefit by the hemodynamic effects of the compounds of the invention, such as the positive inotropic effect or decrease in peripheral vascular resistance and increase in cardiac output; or in those patients in which the negative inotropic effects of the commonly used antiarrhythmic agents is disadvantageous or contraindicated. The versatility of the compounds of the invention and the unusual aspects of the invention are well illustrated by the above.

The compounds of the invention have a combination of beneficial properties generally associated or described as properties or effects on the cardiovascular system of mammals, both humans and animal. These properties may include a positive inotropic effect which can to varying degrees, in accordance with the invention, be associated (or accompanied by) other beneficial effects on the cardiovascular system like decreased in diastolic arterial pressure, decrease in total peripheral resistance and others described above.

Other effects of the compounds of the invention are physiologically distinct from the other beneficial properties; for instance the antiarrythmic effect, the capability of controlling, minimizing, alleviating or preventing circulatory shock in a mammal (such shock having as its symptom a decrease on blood flow and/or oxygen supply).

In a further embodiment of the invention it has been discovered that the compounds of the invention may exert a wide and variable spectrum of properties. Thus, while some compounds of the invention have no observable positive inotropic effect and yet effect a decrease in heart rate or arterial pressure, other compounds which have a positive inotropic effect either decrease the heart rate or have no measurable effect. These compounds are selective in that they exhibit some properties and do not measurably exhibit other properties at the dosage at which they were tested in the experiments described hereinafter.

Other embodiments of the invention are or will become apparent from the disclosure.

The compounds of the invention are berberines, more specifically protoberberines, as further described herein with reference to Formula I.

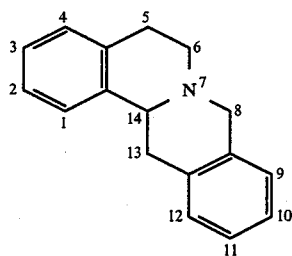

Following traditional nomenclature the rings are identified from A to D and the numbering of the carbon atoms is as illustrated in Formula I. The term protoberberine also herein includes the protoberberines known as tetrahydroprotoberberines and retroberberines, quaternary ammonium protoberberines, dihydroberberines, tetrahydropseudoberberines and dihydroprotoberberines. In the protoberberine alkaloids of the invention, substituents can be present at the C-2 and C-3 and either C-9 and C-10 or at C-10 and C-11 positions. In certain instances there is also substitution at the C-1, C-7, C-8, C-13 and C-14 positions.

The preferred compounds of and used in the invention may be represented by the following Formula II.

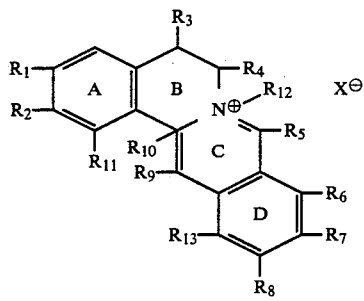

in which:

$R_1$ and $R_2$ may be the same or different and represent hydrogen, hydroxy, preferably a lower alkyl like methyl or a lower alkoxy like methoxy or ethoxy, aryloxy containing generally no more than 12 carbons, but preferably 6 or 7 carbons like phenyloxy or benzyloxy, or when taken together $R_1$ and $R_2$ form an alkylene dioxy like a methylene dioxy group;

$R_3$ represents hydrogen, hydroxyl, preferably a lower alkoxy like methoxy or ethoxy or an aryloxy as described for $R_1$ or $R_2$;

$R_4$ represents hydrogen or preferably a lower alkyl like methyl;

$R_5$ represents hydrogen, preferably a lower alkyl like methyl, aryl like phenyl, arylalkyl (preferably where the alkyl is a lower alkyl) like benzyl, substituted lower alkyl like —CH$_2$(CO)CH$_3$, or oxygen;

$R_6$ and $R_7$ may be the same or different and represent hydrogen, hydroxy, preferably a lower alkoxy like methoxy or ethoxy, aryloxy containing generally no more than 12 carbons, but preferably 6 or 7 carbons like phenyloxy or benzyloxy, carbamoyl —O(CO)NR$_{14}$R$_{15}$ when $R_{14}$ and $R_{15}$ are the same or different and represent hydrogen, preferably lower alkyl like methyl or ethyl, or aryl like phenyl, or when taken together $R_6$ and $R_7$ form an alkylene group like a methylene dioxy group;

$R_8$ represents hydrogen, hydroxyl, preferably a lower alkoxy like methoxy or ethoxy, aryloxy containing no more than 12 carbons, but preferably 6 or 7 carbons like phenyloxy or benzyloxy;

$R_9$ represents hydrogen, lower alkyl like methyl, ethyl, lower alkyl substituted with hydroxyl like CH$_2$OH, hydroxyl, lower alkylene containing generally no more than 6 or 7 carbons like CH$_2$CH=CH$_2$ or CH$_2$CH$_2$CH=CH$_2$, arylalkyl (preferably where the alkyl is a lower alkyl) like benzyl, or oxygen;

$R_{10}$ represents hydrogen or an alkyl, like lower alkyl, like methyl;

$R_{11}$ represents hydrogen, hydroxyl, preferably lower alkoxy like methoxy or ethoxy;

$R_{12}$ represents hydrogen, lower alkyl like methyl or oxygen;

$R_{13}$ represents —CHO or an hydroxy alkyl, like hydroxy methyl.

Ring B may be unsaturated between carbons 5 and 6.

Ring C may be saturated between carbon 8 and the nitrogen and it may also be saturated between carbon 13 and 14 to yield a tetrahydroberberine. Other degrees or positions of the saturation or unsaturation are possible.

The isomers are considered within the generic formula and the specific embodiment contemplates either the d,l-racemic mixture of the compounds or the specific d- or l- resolved form of the compound. It is contemplated that all forms of these racemates must be always of the same potency in all respects.

$X^-$ in the formula represents a biologically acceptable, especially a therapeutically acceptable, anion such as to form salts of the compounds illustrated including the quaterary ammonium salts and the addition salts of organic or inorganic acids. Illustrative acids are inorganic strong acids like sulfuric, nitric, ethanedisulfonic, phosphoric, hydrochloric, hydrobromic, fluorosulfonic, mono-, di- or tri-organic acids like citric, lactic, tartaric, sulfamic, succinic, fumaric, maleic, aliphatic or aromatic acids like benzoic, acetic and numerous others.

It will be noted that it is also within the contemplation of the invention that biological metabolite(s) resulting from the compounds of the invention, are also within the invention, which metabolites are responsible for the positive inotropic effect and/or at least one of the beneficial properties disclosed here. These compounds may or may not evidence a positive inotropic effect, but evidence one or more of the other effects.

The definition of compounds of the invention includes such metabolites.

The invention also contemplates adding to the ring(s) or elsewhere or replacing one or more of the above named substituents by one or more halogens, like chlorine or other therapeutically beneficially active substituents which enhance or otherwise potentiate one or more of the desired properties of the compounds of the invention. Likewise, any of the above substituents can be an ester, an amido, amino, or other functional group which will have a desired therapeutic effect. Such a group may be inert, decrease one of the therapeutic effects (if this is desired) or a side effect (if one is noted which may be less desirable) or increase a particularly desirable one. All such compounds are intended and are contemplated and in the compounds of the invention.

It will be noted that certain subgroups or classes of compounds are preferably if certain therapeutic effects are especially sought after, whereas other classes or subclasses will be preferred if other therapeutic effects are especially sought after. Since the compounds of the invention have several types of therapeutic effects it will be apparent to one skilled in the art that the selection of the special species will depend in a certain measure on what effect is sought after most.

The description of the preparation of many of the compounds of the invention can be found in the chemical and biological literature. General syntheses for the aromatic protoberberines are disclosed in U.S. Pat. No. 3,910,938 and for the tetrahydro compounds in U.S. Pat. Nos. 3,272,707 and 3,426,027. The synthesis of tetrahydropalmatine methiodide, a typical quaternary ammonium salt is described by Narosimham and Bhide, *Chem. Ind.* (London), p. 621 (1969). Among the acceptable salts are the sulfate, nitrate, phosphate, citrate, acetate, maleate, lactate, tartrate, succinate, chloride, bromide, iodide, fluorosulfonate, benzoate and the like. The salts are prepared by methods known in the art.

Of interest, if further details with respect to synthesis or other aspects are needed for one skilled in the art, reference is made to *Shamma Isoquinoline Alkaloids Chemistry and Pharmacology*, Academic Press, New York, 1972 ("Shamma") and Tetsuji Kametani, *The Chemistry of Isoquinoline Alkaloids*, 1969. Hirokawa Publishing Co., Tokoy, Elsiver Publishing Co., New York, (especially chapter 10), both books being incorporated herein by reference.

Among the isoquinoline compounds of particular interest are the following classes: the protoberberines and retroprotoberberines, the protopines which are identifiable by $R_{10}$ representing an oxygen as illustrated in *Shamma*, chapter 18; the rhoedines and papaverrubines, the homoprotoberberines, as shown in *Shamma*, chapter 27. For purposes of this invention, the term berberine is generic to proto- and to homoberberines.

Typical compounds used in accordance with the invention are the following: berberrubine, berberine (umbellatine), d-tetrahydropalmatine, discretine, xylopinine (1-norcoralydine), stepharotine, capaurimine, capaurine, ophiocarpine, dehydrothalictrifoline, dehydrocoryadaline, thalictricavine, thalictrifoline (base III), isocorybulbine, alborine, oxyberberine, 13-allylberberine, norcoralyne, N-methyl-7,8-dihydro-13-methylberberine, palmatine, 13-methylberberine, 13-benzylberberine, 13-hydroxyberberine, coreximine, jatrorrhizine, berberine acetone, and others disclosed herein.

The salts are generally a more convenient form for use. In practice the use of the salt form amounts to use of the base form. Pharmaceutically or biologically acceptable salts are salts whose anions are relatively innocuous to the animal organism in dosages used so that the cardiotonic or other desirable effect of the free base is not vitiated by the effects of the anions.

Mixtures of the compounds of the invention and of their salts may also be used as is contemplated within the invention. It is not within the contemplation of the invention that one skilled in the art should be able to avoid the spirit and scope of the invention by the use of a different salt or a different compound.

In clinical practice said compound or salt thereof will normally be administered orally or parenterally in a wide variety of dosage forms.

Solid compositions for oral administration include compressed tablets, pill, powders, and granules. In such solid compositions, at least one of the active compounds is admixed with at least one inert diluent such as starch, calcium, carbonate, sucrose or lactose. These compositions may also contain additional substances other than inert diluents, e.g., lubricating agents, such as magnesium stearate, talc and the like.

As is known in the art, liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

As is known in the art, preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

As is known in the art, they can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

As has been discussed above, the percentages of active components in the said composition and method for increasing cardiac contractility and the other properties can be varied so that a suitable dosage is obtained. The dosage administered to a particular patient is variable, depending upon the clinician's judgment using the following as criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf. Like criteria shall guide the veterinarian.

It is within the contemplation of the invention as already referred to above, to selectively substitute or add to the rings, selected substituents which favorably influence the desired properties of the compounds and compositions used in the instant invention.

The pharmacological and cardiovascular data of the compounds of the invention was obtained following the protocols described below, which are generally of the standard traditionally accepted type.

Certain terms are commonly used to describe the mechanical properties of cardiac muscle. For definition reference is invited to *Braunwald*, pages 431–452, which is incorporated herein by reference.

The usefulness of the compounds of the invention as positive inotropic agents, (and other uses as disclosed) is demonstrated by effectiveness in standard pharmacological test procedures, for instance in causing a significant increase in the cardiac contractile force in the anesthesized dog with virtually no increase or decrease in heart rate and blood pressure. Protocols used are described herein or by reference to standard medically accepted publications.

The term "contractility" or "inotropic state" has a different meaning than performance.

The term "contractility" is useful to identify a change in contractility (or inotropic state) of the heart as an alteration in cardiac performance that is independent of changes resulting from variations in preload or afterload. When loading conditions remain constant, an improvement in contractility will augment cardiac performance (a positive inotropic effect) while a depression in contractility will lower cardiac performance (a negative inotropic effect). The basal level of contractility is reduced in chronic myocardial failure.

The experimental work was carried out as follows: Healthy adult mongrel dogs (20–30 kg) of both sexes were anesthetized with intravenous sodium pentobarbital (25 mg/kg). Catheters were placed under fluoroscopic control to record left ventricular and aortic pressures. Cardiac outputs were determined by the thermodilution technique. Heart rate (HR) was calculated using electrocardiographic recording, lead aVF. All parameters were recorded on a Gould polygraph.

The dogs were randomly assigned either to the control or to the treated group. The dogs in the control group were infused with a placebo, namely, the vehicle used for the drug tested.

The protoberberine to be tested was administered to these close chest anesthesized dogs at a constant dose for 40 minutes.

During the first 30 minutes the systolic arterial pressure was permited to vary, thereafter the systolic arterial pressure was maintained constant to accurately establish the changes in contractility since dP/dt is pressure dependent. This was accomplished by using a reservoir full of blood under constant pressure connected to the femoral artery.

To study the antiarrhythmic properties, both the control and the protoberberine treated dogs that were studied hemodynamically received ouabain. Ouabain was administered 0.04 mg/kg intravenously as a bolus, followed by a continuous infusion of 0.0006 mg/kg/min. The antiarrhythmic properties were assessed by comparing the control and the protoberberine treated group using as a parameter the time of appearance of premature ventricular beats and the time of appearence of ventricular tachycardia.

Jatrorrhizine was infused at a dose of 0.2 mg/kg/min. After 35 minutes the left ventricular dP/dt was increased by about 35% while the diastolic aortic pressure decreased. This suggests that an increase in contractility as well as peripheral vasodilation occured. The heart rate and systolic aortic pressure remained the same. No antiarrhythmic properties were observed.

13-Hydroxyberberine chloride (berberine phenol betaine hydrochloride) was infused at a rate of 0.2 mg/kg/min. There was a possible increase in the left ventricular dP/dt suggesting an increase in contractility. No change in heart rate, diastolic or systolic aortic pressure was measurable. No antiarrhythmic activity was observed.

Likewise 13-hydroxyberberine bromide produces similar effects in the preceding experiment.

7,8-Dihydro-13-methylberberine N-methyl fluorosulfonate in a dose of 0.2 mg/kg/min showed unchanged dP/dt when blood pressure was maintained constant. This compound therefore showed no inotropic properties, either positive or negative. At the same time however the heart rate decreased significantly by 32%. Therefore, this compound possesses potent bradycardic effects which may be favorable especially in patients with tachycardia which is common in certain cardiovascular diseases. The experiments also show a fall in diastolic aortic pressure by 26% suggesting a vasodilating effect. Therefore this drug shows no changes in inotropy, but a negative chronotropic effect and a vasodilatory effect. These types of properties may be also useful in the treatment of heart failure since they permit an increase in left ventricular function. No antiarrhythmic activity was observed.

Berberine acetone, when infused at a rate of 0.5 mg/kg/min increased left ventricular dP/dt by 60% therefore demonstrating a positive inotropic effect. At the same time there was no measurable change in heart rate or systolic aortic pressure. Diastolic aortic pressure fell by 20%, cardiac output increased by 40%, while total peripheral resistance dropped by 30%, which suggests a mild vasodilatory effect. Therefore, this drug shows an intense increase in contractility, but a mild vasodilatory effect. Both effects increase cardiac performance. No antiarrhythmic effect was observed.

13-Allylberberine bromide when given at a rate of 0.2 and 0.5 mg/kg/min, increased left ventricular dP/dt significantly by 28% and decreased heart rate and diastolic arterial pressure mildly by about 20% and 26% respectively. Contrary to the previously described compounds, this compound does have antiarrhythmic effects. Therefore, this compound has a favorable effect on cardiac performance and also on arrhythmias.

Other pharmaceutically acceptable salts of 13-allylberberine bromide produce similar effects in the preceding experiment.

Palmatine chloride was given at a dose of 0.2 mg/kg/min. It showed a mild increase in left ventricular dP/dt and a mild effect of decreasing diastolic aortic pressure by about 15%. The compound also exhibited a possible antiarrhythmic effect. No change in heart rate was observed.

Similar effects are obtained with other pharmaceutically acceptable salts of palmatine.

Coreximine was infused at a rate of 0.2 mg/kg/min to 8 dogs. It showed an increase in left ventricular dP/dt of 32%, a decrease in heart rate of 17%, and also a decrease in diastolic arterial pressure.

13-Benzylberberine bromide was given at a dose of 1 mg/kg/min to 10 dogs. The left ventricular dP/dt increased by 135% showing a striking increase in contractility. dP/dt increased gradually during the infusion of this compound which is contrary to the results with berberine where the contractility plateaus at around an increase of 40% independently of the dosage given. At the same time heart rate did not change noticeably. Diastolic arterial pressure fell progressively by about 38%. Total peripheral resistance decreased by 50% which is a marked fall. Cardiac output increased by 70%. Therefore this compound has a very potent inotropic effect as well as a very potent vasodilatory effect. As a consequence, there is a marked increased cardiac output. The compound has possible antiarrhythmic properties.

The compounds of the invention may also be administered orally. When this is done the compounds are given in a single dose (unless stated differently). The parameters are measured at 15 minute intervals starting at least 1 hour before dosing in order to establish a baseline.

When the compounds are given orally, they are given to conscious dogs which have been instrumented at least two weeks previous to the experiment.

These dogs were instrumented with an electromagnetic flowmeter placed around the ascending aorta to measure cardiac output, with catheters in the left ventricle and the aorta for recording of their respective pressure. All these parameters together with left ventricular dP/dt and lead aVF of the electrocardiogram were recorded during the experiments continuously at a speed of 1 mm/second and at 15 minute intervals at a speed of 200 mm/second.

Coreximine was given orally at doses of 0.25, 0.5 and 5 mg/kg. Each dose was studied in 6 dogs. At a dose of 5 mg/kg the total amount of the compound delivered approximates the amount delivered by infusion at 0.2 mg/kg/min for 30 minutes (6 mg/kg).

The dose of 0.25 mg/kg was only mildly effective. At the dose of 0.5 mg/kg, the left ventricular dP/dt increased by about 30% from $2618\pm221$ to $3556\pm371$ mm Hg/sec (P 0.05). Cardiac output increased significantly from $2.4\pm0.1$ to $2.9\pm0.1$ l/min (P 0.01) and left ventricular and diastolic pressure fell from $6.7\pm0.8$ to $5.8\pm0.6$. At the same time mean arterial pressure increased by 20 mm of Hg while heart rate increased from 73 to 94 beats per minute. Therefore, oral coreximine, even at a very low dose, is a positive inotropic agent improving left ventricular performance and is well absorbed orally. It should be noted, however, that there was some increase in heart rate and blood pressure.

At the higher dose of 5 mg/kg, which corresponds to 0.17 mg/kg/min, the dP/dt increased from $2559\pm76$ to $4630\pm378$ mm Hg/sec (P 0.005), an increase of about 80%. The systolic arterial pressure increased from 125 to 168 mm Hg while the diastolic arterial pressure increased from 78 to 106 mm Hg. Heart rate increased from 83 to 133. Therefore, while heart rate and blood pressure increased, the dP/dt increased markedly. The cardiac output increased from $2.2\pm0.1$ to $2.6\pm0.1$ (P 0.005) and total peripheral resistance increased by 22%. Left ventricular and-diastolic pressure fell from $6.4\pm0.6$ to $4.4\pm0.7$ (P 0.05).

Thus, coreximine increased strikingly contractility, decreased the preload and increased cardiac output thus augmenting performance while increasing arterial pressure and heart rate.

The data, which shows an increase in heart rate and increase in arterial pressure when coreximine is administered orally in contrast to a decrease in these two effects when the drug is administered intravenously suggests that the increase in the heart rate and arterial pressure is due to the bitterness of the berberine derivatives or some other outside influence. In the above experiments the natural bitterness of coreximine was not masked by conventional mean known to those skilled in the art.

Next, coreximine was given orally to dogs that were pretreated with propanolol at a dose of 1 mg/kg. Propanolol was given to verify whether coreximine has a beta adrenergic agonist activity, specifically to verify whether the increased in contractility measured by dP/dt max and dP/dt at 40 mm Hg of developed pressure would disappear. It was found that the increase in contractility does not disappear after this beta blockade and therefore the increase in contractility is not due to beta angonist effects either of the drug itself or other external influences. The increases in blood pressure also were not nullified; however, increases in blood pressure are alpha and not beta mediated.

In another experiment, 13-allylberberine bromide was given orally to conscious dogs at a dose of 5 and of 50 mg/kg. Each dose was given to 5 dogs. The compound is effective orally when given 50 mg/kg but not when given 5 mg/kg. When given 50 mg/kg it increased dP/dt significantly from 2561 to 3391 mm Hg/sec showing a marked positive inotropic property. Also, cardiac output increased from 2.3 to 2.7 l/min and left ventricular end-diastolic pressure fell from 5.8 to 4.5 mm Hg showing an improvement in ventricular performance and a reduction in preload. Heart rate increased from 69 to 81 and mean arterial pressure from 90 to 116 mm Hg. The increase in heart rate and arterial pressure again suggests the influence of the bitterness of the drug.

Moreover, when 2 doses of 13-allylberberine bromide 50 mg/kg were given orally with an interval of 30 minutes between them dP/dt increased from 2500 to 4600 mm Hg, an increase of 84% showing that higher or multiple dose may be more effective.

Similarly other pharmaceutically acceptable salts of 13-allylberberine produce equivalent effects.

13-Methylberberine citrate given 50 mg/kg orally in 2 dogs increased left ventricular dP/dt by an average of 27% suggesting that this compound was absorbed when given orally. When it was given intravenously 0.2 mg/kg/min for 30 minutes its effect was similar suggesting around a 10:1 intravenous to oral ratio of effectiveness.

Berberine tartrate (5 mg/kg) given orally to 2 dogs increased left ventricular dP/dt by 17%.

None of the above mentioned compounds caused arrhythmias. The compounds of the instant invention have either an antiarrhythmic effect or no observable effect on arrhythmias at the dosage at which the compounds are administered in the above experiments. Typical therapeutic compositions of the invention may include the smallest amount capable of causing the desired therapeutic effect to an amount which gives the optimum desired effect. Larger amounts would tend to be unnecessary. Typical therapeutic compositions of the invention may include from about 0.01% or preferably 0.1% by weight of active ingredient, that is, a positive inotropic compound of the invention, the balance of the composition being either a biologically-acceptable inert carrier and/or any other known or yet unknown biologically-active ingredient.

More commonly the biological compositions of the invention will have from about 0.1 to about 99.9% by weight of the active ingredient, based on the total weight of the composition. Under certain conditions, the compositions of the invention may contain from 0.5 to about 50% of the active ingredient by weight of the total composition. For some applications, the compositions of the invention, will include from a minimum of about 0.25 to 0.50 to a maximum of about 99.75 to 99.50, or within the range of 1 to 99% of active ingredient to total weight of the composition. Since the active ingredient of the invention, has numerous therapeutic effects, in addition to the positive inotropic effect, it will be appreciated by one skilled in the art that the content of the active ingredient can vary considerably. Furthermore, as apparent from the teaching of the specification, the positive inotrope of the invention is useful to treat various cardovascular conditions. Therefore this will be another reason for adapting the concentration of the positive inotrope in the composition supplied to the patient in accordance with accepted standards of the medical profession.

It is of course understood by one of average skill in the art that any other ingredient may be part of the biologically-active composition such as slow or timed-release ingredients, or other biologically-active ingredients. It is to be understood of course that the percentage of active ingredient in the total composition may depend as is well known for one skilled in the art, on whether or not the composition is intended for oral or parenteral or other type of administration.

For therapeutic use in combination with cardiac glycosides such as digitalis, it is desirable that the glycoside be present in the composition in an amount from about 1% to about 99% by weight and if desired from 10 to 90% by weight, based on the weight of berberine and/or protoberberine alkaloid present, and preferably in an amount of from about 30% to 60% by weight. Generally, amounts of active ingredient toward the upper end of the ranges are used in compositions for the therapeutic treatment of emergency cardiovascular disorders such as circulatory, hypovolemic, or cardiogenic shock, while amounts of active ingredient toward the lower end of the ranges are used in compositions for the treatment of chronic cardiovascular diseases such as congestive heart failure and chronic cardiac arrythmias.

However, the relative amounts of the berberine and/or other protoberberine will vary with respect to the cardiac glycoside such as digitalis, over a wide range depending on the indication sought to be therapeutically treated and other circumstances with which one skilled in the art is quite familiar. As has been noted in the specification, an unexpected advantage of the berberine and other protoberberines of the invention is that they remarkably widen the therapeutic index of a cardiac glycoside such as digitalis. With that consideration in mind, the amount of berberine or other protoberberine compound which is used in conjunction with the cardiac glycoside (such as digitalis) may often be designed to maximize both the effect of the berberine (or other protoberberine compound) and of the cardiac glycoside. It is of course understood that such therapeutic consideration may lead to a certain amount of compromise between the two optimum effects sought to be accomplished with respect to the patient. Nonetheless the full advantage of the berberine (or protoberberine compound) can be suitably designed by one of average skill in the art in the treatment sought to be attained for the individual patient.

Other dosages and forms of administration are described below.

a. Berberine given intravenously (i.v.) as a continuous infusion: 0.0001 to 1 mg/kg of body weight/minute; to be given as a continuous intravenous infusion a period of 1 minute to 24 hours in a one day period. Preferred dose 0.005 to 0.2 mg/kg body weight/min. It should be kept in mind that the amount of berberine and the speed of its infusion will depend on the desired length of infusion. Other factors that may influence the dose of berberine per dose, per day period, per kilogram of body weight and the speed of infusion may be the severity of the condition to be treated (e.g. heart failure), the condition of the myocardium, the functional state of the kidneys and the liver and concomitant use of other drugs. A suitable composition for i.v. administration may contain from about 1 to 5% of the active ingredient to the total liquid composition.

b. Berberine given intravenously as a bolus or intramuscularly or subcutaneously or transdermally: 0.001 to 200 mg/kg of body weight, given from once a week up to every 2 hours. Preferred dose 0.005 to 1 mg/kg of body weight. The amount of drug per dose may depend on the same factors mentioned above: frequency of administration, severity of the condition to be treated (e.g. heart failure), the condition of the myocardium, functional conditions of the kidneys and the liver and concomitant use of other medications.

c. Berberine given orally or buccally or sublingually: 0.0 to 1000 mg/kg of body weight per dose. One dose can be given once per week up to twelve doses per day. Preferred frequency one to four doses per day. Preferred is a dose of 0.1 to 100 mg per dose.

d. When berberine is given with any other drug for treatment of a pathologic condition such as heart failure (such drugs as cardiotonics, inotropic agents, digitalis, other glycosides, vasodilators, angiotensin-converting-enzyme inhibitors and duretics), berberine may be given in the same dose as when given alone or will be given in a dose up to about 100 times smaller. The other drug may be given in the same dose as when it is given alone or in a dose up to about 100 times smaller. The ratio between berberine and the other drug will vary according to the usual dose of this other drug. Thus, when used with drugs of the digitalis glycoside type such as Digoxin and Ouabain, these latter will be given in their usual dose: 0.125 to 1.0 mg per day for Digoxin and 0.01 to 0.03 mg/kg of body weight for the digitalization dose of Ouabain. The ratio therefore between berberine on the one hand and Digoxin or Ouabain on the other hand, may vary between 1 to 1000 and 1000 to 1 either per dose or per day. The preferred ratio of berberine/Ouabain or berberine/DigoXin is from 100/1 to 1/10. This ratio may depend on the factors mentioned above and on the pharmacokinetics of the drugs involved (e.g. in patients with reduced kidney function the dose of digitalis type compounds should be decreased). The factors that influence the dose of berberine are the same as those under item "b".

e. The dose of all other compounds described above have the same range as those of berberine related above in items "a" to "d". What has been described herein with respect to berberine applies equally to coreximine. Likewise, other typical compounds of the invention are administered in like dosages. Such compounds include specifically berberrubine, berberine (umbellatine), d-tetrahydropalmatine, discretine, xylopinine (1-norcoralydine), stepharotine, capaurimine, capaurine, ophiocarpine, dehydrothalictrifoline, dehydrocoryadaline, thalictricavine, thalictrifoline (base III), isocorybulbine, alborine, oxyberberine, 13-allylberberine, norcoralyne, N-methyl-7,8-dihydro-13-methylberberine, palmatine, 13-methylberberine, 13-benzylberberine, 13-hydroxyberberine, jatrorrhizine, berberine acetone, and others disclosed herein.

Useful oral, buccal, sublingual and transdermal dose of these compounds will depend on the bioavailability of each drug through these routes. Thus, coreximine may be absorbed better than berberine when given orally and consequently the needed dose will be smaller. Other compounds of this family that also do not have a quarteriary $NH_4$ group may be administered in similar dosages to coreximine.

Other variations will become readily apparent to one of average skill in the art without undue experimentation.

I claim:

1. A therapeutic positive inotropic composition for increasing contractility of the heart as shown by a positive inotropic effect which comprises a biologically acceptable carrier and in an amount effective to cause a positive inotropic effect, (a) digitalis and (b) a compound selected from the group consisting of coreximine and the pharmaceutically acceptable salts thereof, the composition being effective to cause such a positive inotropic effect.

2. The composition of claim 1 which includes digitalis and is for oral administration.

3. The composition of claim 2 whewrein the digitalis is selected from the group consisting of digoxin and ouabain.

4. The composition of claim 1 wherein the ratio between the compound and digitalis is in the range from 100 to 1 to 1 to 10.

5. A therapeutic method of increasing the contractility of the mammalian heart as shown by a positive inotropic effect thereon which comprises administering to a mammal in need thereof in an amount effective to cause a positive inotropic effect, a composition which comprises a biologically acceptable carrier and a compound selected from the group consisting of (a) coreximine and the pharmaceutically acceptable salts thereof and (b) digitalis, causing a positive inotropic effect over a wider thereapeutic index than by administration of digitalis alone.

6. The therapeutic method of claim 5 wherein the compound is administered orally.

7. The therapeutic method of claim 5 wherein the composition is administered by intravenous infusion.

8. A therapeutic method of increasing the contractility of the mammalian heart as shown by a positive inotropic effect thereon which comprises administering orally to a mammal in need thereof in an amount effective to cause a positive inotropic effect, a composition which comprises a biologically acceptable carrier and a compound selected from the group consisting of (a) coreximine and the pharmaceutically acceptable salts thereof and (b) digitalis, causing a positive inotropic effect over a wider thereapeutic index than by administration of digitalis alone, the ratio of (a) to (b) being in the range from about 100 to 1 and 1 to 10.

9. The therapeutic method of claim 8 wherein the digitalis in the composition is selected from the group consisting of ouabain and digoxin.

10. The method of claim 9 wherein the dosage of the administered composition per kg of body weight per day is 0.125 to 1.0 mg for digoxin and 0.01 to 0.03 mg for ouabain.

11. The composition of claim 1 wherein the compound is present in the range form about 0.01% to about 99.9% by weight of the composition.

12. The method of claim 5 wherein the compound is administered in an amount in the range from about .001mg to about 100 mg per kg of body weight per dose.

13. The method of claim 8 wherein the compound is administered in an amount in the range from about 0.001 mg to about 100 mg per kg of body weight per dose.

14. The composition of claim 1 wherein the digitalis is present in the range from about 1% to about 99% by weight of coreximine.

15. The composition of claim 14 wherein the digitalis is present in the range from about 30% to about 60% by weight of coreximine.

* * * * *